(12) United States Patent
Smith et al.

(10) Patent No.: US 8,267,091 B2
(45) Date of Patent: Sep. 18, 2012

(54) PATIENT INTERFACES

(75) Inventors: Nicholas Charles Alan Smith, Auckland (NZ); Lewis George Gradon, Auckland (NZ); Alastair Edwin McAuley, Auckland (NZ); Christopher Earl Nightingale, Lodon (GB); Ivan Milivojevic, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 0 days.

(21) Appl. No.: 12/536,656

(22) Filed: Aug. 6, 2009

(65) Prior Publication Data
US 2010/0024825 A1 Feb. 4, 2010

Related U.S. Application Data

(60) Continuation of application No. 10/916,700, filed on Aug. 12, 2004, now Pat. No. 7,874,292, which is a division of application No. 10/293,637, filed on Nov. 13, 2002, now Pat. No. 6,892,729.

(30) Foreign Application Priority Data

Nov. 20, 2001 (NZ) ........................................ 515577

(51) Int. Cl.
*A62B 9/04* (2006.01)
*A62B 7/00* (2006.01)
*A62B 18/02* (2006.01)
*A62B 9/02* (2006.01)
*A62B 7/10* (2006.01)
*A62B 18/08* (2006.01)

(52) U.S. Cl. ......... 128/207.18; 128/202.27; 128/205.11; 128/205.24; 128/205.25; 128/911; 128/205.29; 128/206.27; 128/206.28

(58) Field of Classification Search ............. 128/202.27, 128/205.11, 205.25, 205.24, 911, 205.29, 128/206.27, 206.28, 207.18
See application file for complete search history.

(56) References Cited

U.S. PATENT DOCUMENTS

| 3,670,726 A | 6/1972 | Mahon et al. |
| 4,676,241 A | 6/1987 | Webb et al. |
| 4,774,940 A | 10/1988 | Linder |
| 4,938,209 A | 7/1990 | Fry |
| 5,694,922 A | 12/1997 | Palmer |
| 5,921,239 A | 7/1999 | McCall et al. |
| 5,937,851 A * | 8/1999 | Serowski et al. ........ 128/202.27 |

(Continued)

FOREIGN PATENT DOCUMENTS
WO 98/34665 8/1998

*Primary Examiner* — Patricia Bianco
*Assistant Examiner* — Nihir Patel
(74) *Attorney, Agent, or Firm* — Knobbe, Martens, Olson & Bear, LLP

(57) ABSTRACT

The present invention relates to a device for delivering a supply of gases to a patient. The device includes a patient interface and connecting member. The connecting member is preferably a L-shaped swivelled connector that is capable of being fixed into one of two positions, a first position where the connector is freely rotatable within the patient interface, and a second position where an interference between the interface and connector prevents the free rotation of the connector within the patient interface. The present invention further relates to a connector that has outlet means, which includes at least one outlet vent and a funnel, which in use directs and passes a substantial portion gases expired from the patient through the outlet vent or vents.

21 Claims, 12 Drawing Sheets

U.S. PATENT DOCUMENTS

| | | |
|---|---|---|
| 6,192,886 B1 | 2/2001 | Rudolph |
| 6,491,034 B1 | 12/2002 | Gunaratnam et al. |
| 6,532,961 B1 | 3/2003 | Kwok et al. |
| 6,581,594 B1 | 6/2003 | Drew et al. |
| 6,615,830 B1 | 9/2003 | Serowski et al. |
| 6,823,869 B2 | 11/2004 | Raje et al. |
| 6,851,425 B2 | 2/2005 | Jaffre et al. |
| 6,892,729 B2 | 5/2005 | Smith et al. |
| 7,011,090 B2 | 3/2006 | Drew et al. |
| 7,316,230 B2 | 1/2008 | Drew et al. |
| 2001/0032648 A1 | 10/2001 | Jestrabek-Hart |
| 2002/0023649 A1 | 2/2002 | Gunaratnam et al. |
| 2002/0023650 A1 | 2/2002 | Gunaratnam et al. |
| 2008/0099014 A1 | 5/2008 | Drew et al. |

* cited by examiner

PATIENT INTERFACES

This application is a continuation application of U.S. patent application Ser. No. 10/916,700 filed on Aug. 12, 2004 now U.S. Pat. No. 7,87,4292, which is a divisional application of U.S. patent application Ser. No. 10/293,637 filed on Nov. 13, 2002, now U.S. Pat. No. 6,892,729. Each of these are hereby incorporated by reference in their entirety.

BACKGROUND OF THE INVENTION

1. Field of the Invention

This invention relates to patient interfaces, particularly though not solely for use in providing Continuous Positive Airway Pressure (CPAP) therapy or positive pressure ventilation to patients suffering from obstructive sleep apnoea (OSA).

2. Summary of the Prior Art

In the art of respiration devices, there are well known a variety of respiratory masks which cover the nose and/or mouth of a human user in order to provide a continuous seal around the nasal and/or oral areas of the face such that gas may be provided at positive pressure within the mask for consumption by the user. The uses for such masks range from high altitude breathing (ie. aviation applications) to mining and fire fighting applications, to various medical diagnostic and therapeutic applications.

One requisite of such respiratory masks has been that they provide an effective seal against the patient's face to prevent leakage of the gas being supplied. Commonly, in prior mask configurations, a good mask-to-face seal has been attained in many instances only with considerable discomfort for the user. This problem is most crucial in those applications, especially medical applications, which require the user to wear such a mask continuously for hours or perhaps even days. In such situations, the user will not tolerate the mask for long durations and optimum therapeutic or diagnostic objectives thus will not be achieved, or will be achieved with great difficulty and considerable user discomfort.

Where such masks are used in respiratory therapy, in particular treatment of obstructive sleep apnoea (OSA) using continuous positive airway pressure (CPAP) therapy, there is generally provided in the art a vent for washout of the bias flow or expired gases to the atmosphere. Such a vent may be provided for example, as part of the mask, or in the case of some respirators where a further conduit carries the expiratory gases, at the respirator. A further requisite of such masks is the washout of gas from the mask to ensure that carbon dioxide build up does not occur over the range of flow rates. In the typical flow rates in CPAP treatment, usually between 4 cm H.sub.2O and 20 cm H.sub.2O, prior art attempts at such vents have resulted in excessive noise causing irritation to the user and any bed partners.

Various approaches have been developed in the prior art to attempt to reduce the noise when CPAP therapy is provided. For example, in PCT Patent Application No. WO98/34665 it has been proposed that the vent include a resilient plug with rounded edge apertures to reproduce noise. However, this is not entirely effective in eliminating the extra noise created by a vent at the mask.

In common with all attempts to improve the fit, sealing and user comfort is the need to avoid a concentrated flow of air at any portion of the respiratory tracts. In particular with oral masks or mouthpieces it is a disadvantage of prior art devices that the oral cavity may become overly dehydrated by use of the device, causing irritation and possible later complications.

SUMMARY OF THE INVENTION

It is an object of the present invention to attempt to provide a patient interface which goes some way to overcoming the abovementioned disadvantages in the prior art or which will at least provide the industry with a useful choice.

Accordingly in a first aspect the present invention consists in a device for delivering a supply of gases to a patient comprising or including:

a patient interface fittable to said patients' nose or mouth, which in use is in fluid communication with said supply of gases, connecting member having two ends and interface means, one end of said two ends being locatable within said patient interface and the other end of said two ends is connectable to said supply of gases, said member capable of being fixed into one of two positions, a first position where said member is freely rotatable within said patient interface, and a second position where said interference means prevents the free rotation of said member within said patient interface.

In a second aspect the present invention consists in a continuous positive airways pressure system for delivering gases to a patient comprising or including a pressurised source of gases, transport means, in fluid communication with said pressurised source, adapted to convey said gases, and a nasal mask in fluid communication with said transport means, in use, delivering said gases to said user, said nasal mask comprising or including:

a body portion having an inlet, connected to said transportation means by a connecting member, sealing means engaged with said body portion, and adapted to seal against the facial contours of said patient, and securement means attached to or around the head of said user, wherein said connecting member has two ends and interference means, one end being locatable within said patient interface and the other end of said two ends connectable to said transportation means, said connecting member capable of being fixed into one of two positions, a first position where said member is rotatable within said patient interface, and a second position where said interference means prevents the free rotation of said member within said patient interface.

In a third aspect the present invention consists in a device for delivering a supply of gases to a patient comprising:

a patient interface, which in use is in fluid communication with said supply of gases, connecting member that connects said patient interface with said supply of gases, outlet means associated with said connecting member, said outlet means including at least one outlet vent and a funnel, which in use directs and passes a substantial portion gases expired from said patient through said at least one outlet vent.

To those skilled in the art to which the invention relates, many changes in construction and widely differing embodiments and applications of the invention will suggest themselves without departing from the scope of the invention as defined in the appended claims. The disclosures and the descriptions herein are purely illustrative and are not intended to be in any sense limiting.

BRIEF DESCRIPTION OF THE DRAWINGS

One preferred form of the present invention will now be described with reference to the accompanying drawings in which;

FIG. 15 is an exploded side view of the locking mechanism part of the swivelled elbow connection in the second position.

DETAILED DESCRIPTION OF THE PREFERRED EMBODIMENTS

The present invention provides improvements in the delivery of positive pressure ventilation therapy. In particular a patient interface is described which is quieter for the user to wear and reduces the side leakage as compared with the prior art. The patient interface of the present invention includes improvements to the swivel elbow connector, bias flow directional funnel and/or elbow diffuser. It will be appreciated that the patient interface as described in the preferred embodiment of the present invention can be used in respiratory care generally or with a ventilator but will now be described below with reference to use in a humidified positive pressure ventilation system. It will also be appreciated that the present invention can be applied to any form of patient interface including, but not limited to, nasal masks, oral masks and mouthpieces.

Figure 1:
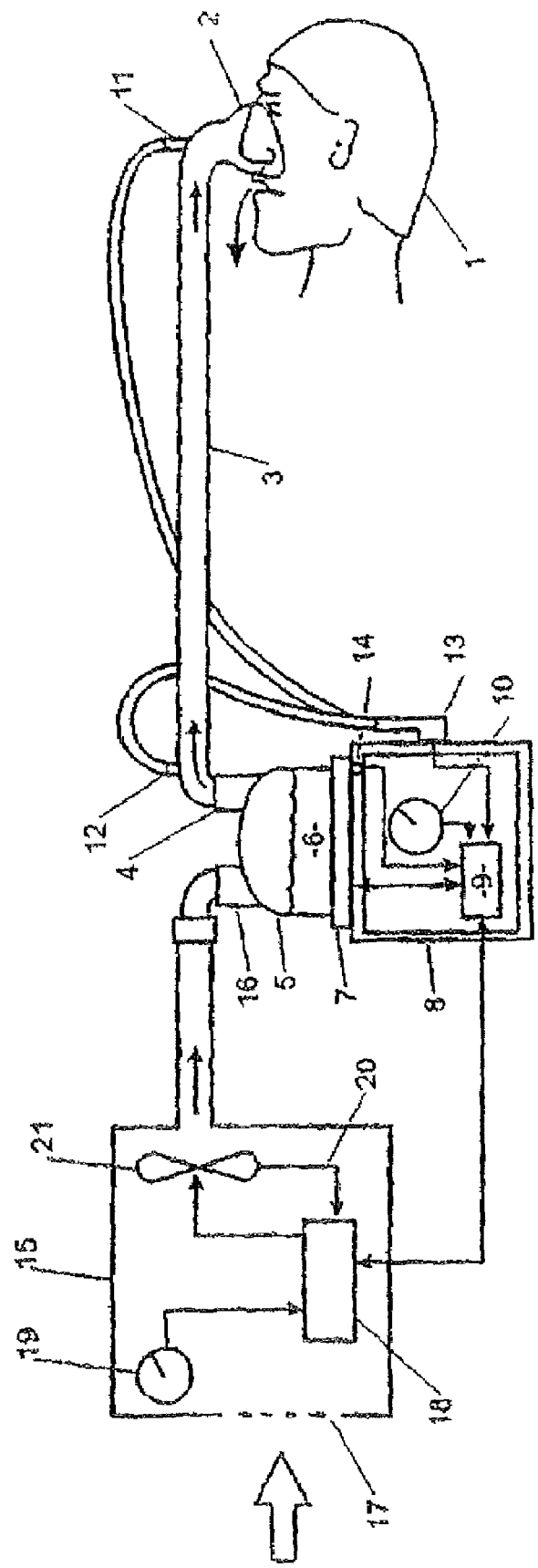
FIG. 1 is a block diagram of a humidified positive pressure ventilation system as might be used in conjunction with the present invention.

With reference to FIG. 1 a humidified positive pressure ventilation system is shown in which a patient 1 is receiving humidified and pressurised gases through a patient interface 2 connected to a humidified gases transportation pathway or inspiratory conduit 3. It should be understood that delivery systems could also be YPAP (Variable Positive Airway Pressure) and BiPAP (Bi-level Positive Airway Pressure) or numerous other forms of respiratory therapy. Inspiratory conduit 3 is connected to the outlet 4 of a humidification chamber 5, which contains a volume of water 6. Inspiratory conduit 3 may contain heating means or heater wires (not shown), which heat the walls of the conduit to reduce condensation of humidified gases within the conduit. Humidification chamber 6 is preferably formed from a plastics material and may have a highly heat conductive base (for example an aluminium base) which is in direct contact with a heater plate 7 of humidifier 8. Humidifier 8 is provided with control means or electronic controller 9 which may comprise a microprocessor based controller executing computer software commands stored in associated memory.

Controller 9 receives input from sources such as user input means or dial 10 through which a user of the device may, for example, set a predetermined required value (reset value) of humidity or temperature of the gases supplied to patient 1. The controller may also receive input from other sources, for example temperature and/or flow velocity sensors 11 and 12 through connector 13 and heater plate temperature sensor 14. In response to the user set humidity or temperature value input via dial 10 and the other inputs, controller 9 determines when (or to what level) to energise heater plate 7 to heat the water 6 within humidification chamber 5. As the volume of water 6 within humidification chamber 5 is heated, water vapour begins to fill the volume of the chamber above the water's surface and is passed out of the humidification chamber 5 outlet 4 with the flow of gases (for example air) provided from a gases supply means or blower 15 which enters the chamber through inlet 16. Exhaled gases from the patient's mouth are passed directly to ambient surroundings.

Blower 15 is provided with variable pressure regulating means or variable speed fan 21, which draws air or other gases through blower inlet 17. The speed of variable speed fan 21 is controlled by electronic controller 18 (or alternatively the function of controller 18 could be carried out by controller 9) in response to inputs from controller 9 and a user set predetermined required value (preset value) of pressure or fan speed via dial 19.

Nasal Mask

Figure 2:
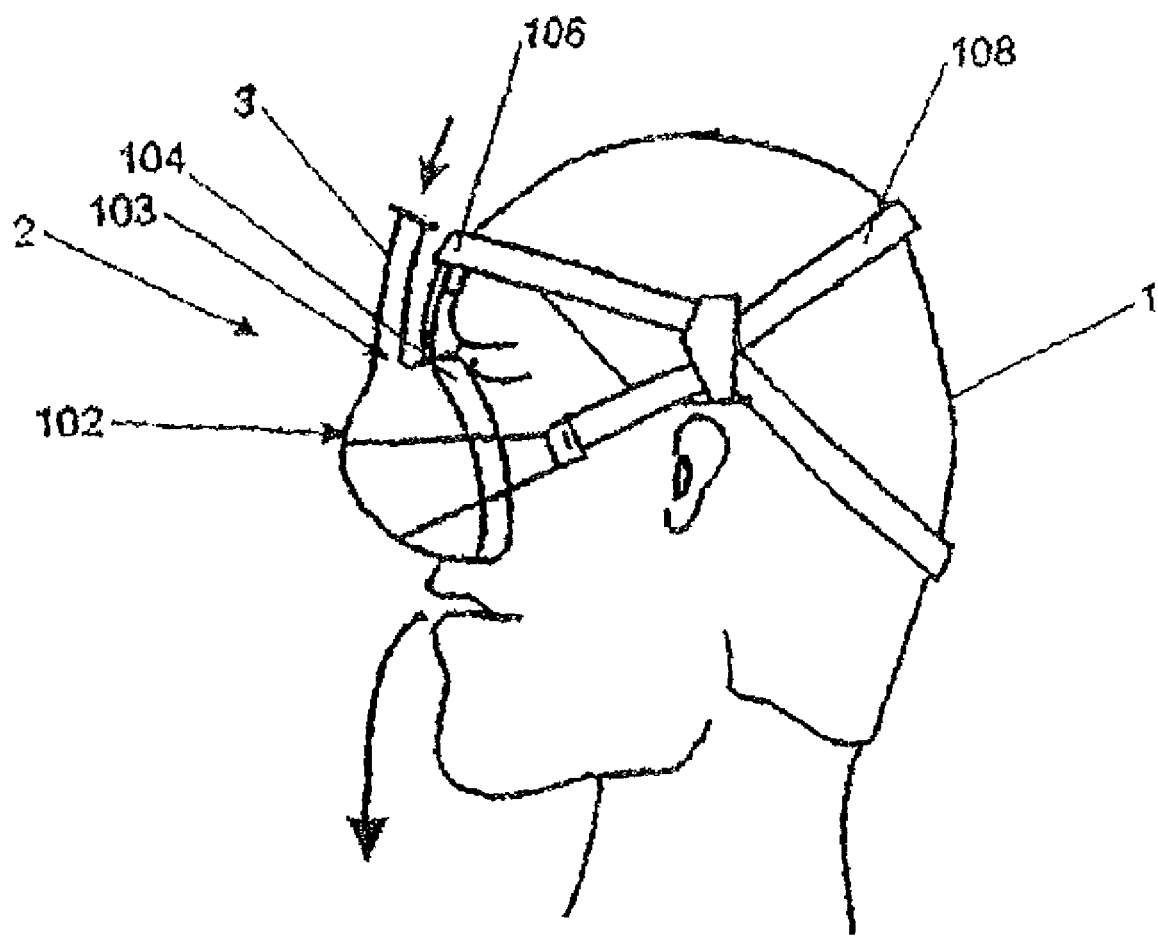
FIG. 2 is an illustration of the nasal mask in use according to the preferred embodiment of the present invention.

A nasal mask that may be used with the improvements to the swivel elbow connector, bias flow directional funnel and/or elbow diffuser of the present invention is shown in FIG. 2. The mask includes a hollow body 102 with an inlet 103 connected to the inspiratory conduit 3. The mask 2 is positioned around the nose of the user 1 with the headgear 108 secured around the back of the head of the patient 1. The restraining force from the headgear 108 on the hollow body 102 and the forehead rest 106 ensures enough compressive force on the mask cushion 104, to provide an effective seal against the patient's face.

The hollow body 102 is constructed of a relatively inflexible material for example, polycarbonate plastic. Such a material would provide the requisite rigidity as well as being transparent and a relatively good insulator.

The improved swivel elbow connector, bias flow directional funnel and/or elbow diffuser of the present invention may also be used with a mouthpiece as described below, or with a full facial mask.

Mouthpiece

Referring to FIGS. 3 to 10 a mouthpiece that may utilise the improvements to the swivel elbow connector, bias flow directional funnel and/or elbow diffuser. In this embodiment, the mouthpiece 50 includes a vestibular shield 49 being a generally flat and generally rectangularly-shaped member in front elevation having a curved profile that reflects the curvature of a patient's jaw and in turn the curvature of the labial vestibule region A gases passageway extends through the vestibular shield from an inlet 51 to an outlet 52 in much the same way as with the earlier embodiments. The inlet 51 is provided by a flattened oval-shaped connector 53. The outlet 52 has an even more laterally extended flattened oval shape 54. Most prominently, the mouthpiece SO includes a tongue depressor 55 extending from the inner face of the vestibular shield 49. The operation of the tongue depressor will be described further on with reference to FIG. 5. The tongue depressor includes a vertical stiffening flange 56 centrally located on its upper surface and extending from the gases outlet 52. In use gases flow easily around the stiffening flange 56 effectively bifurcating the gases outlet 52. The tongue depressor 55 further includes a pair of vertically extending spacers 57, which in use may abut against the roof of the patient's mouth and ensure that the tongue cannot completely block the air passageway. In the mouthpiece 50 the sealing effect of the vestibular shield 49 against the lips of the user is enhanced by providing teeth abutments of significantly increased thickness than the raised area 20 of the earlier embodiments. In particular, an upper teeth abutment 58 and a lower teeth abutment 59 are provided, with the lower teeth abutment 59 protruding further from the inner face of the vestibular shield 49 than the upper teeth abutment 58. This difference serves to match the typical over-bite of most users. The abutments 58 and 59 are not required to be wider than the gases outlet 52.

A notch 60 is provided centrally in the upper edge of the vestibular shield 49 to accommodate the upper frenal attachment. A slight bead 61 is provided around the edge of the vestibular shield 49 for user comfort, with the vestibular shield 49 otherwise being very thin for additional suppleness.

Figure 6:
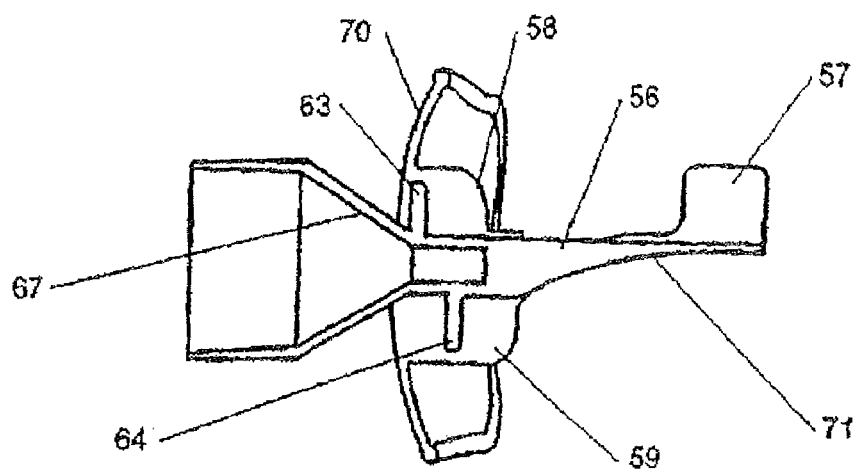
FIG. 6 is a cross-section of the mouthpiece of FIG. 4.

Referring particularly to FIG. 6, the mouthpiece 50 is preferably formed by over-moulding a soft and supple material part 70 over a stiffer material part 67. These can generally be termed the shield part and the passageway-forming insert. The passageway-forming insert preferably includes a pair of upper and lower vertical flanges 63 and 64 to fully engage within the supple material. The passageway-forming insert 67 includes the vertically extending stiffening flange 56 of the tongue depressor 55, together with a curved planar portion 71 forming the backbone of the tongue depressor 55. The vertically extending spacers 57 are of the soft and supple material and are part of the over-moulding 70, as are the upper and lower teeth abutments 58 and 59.

Figure 4:
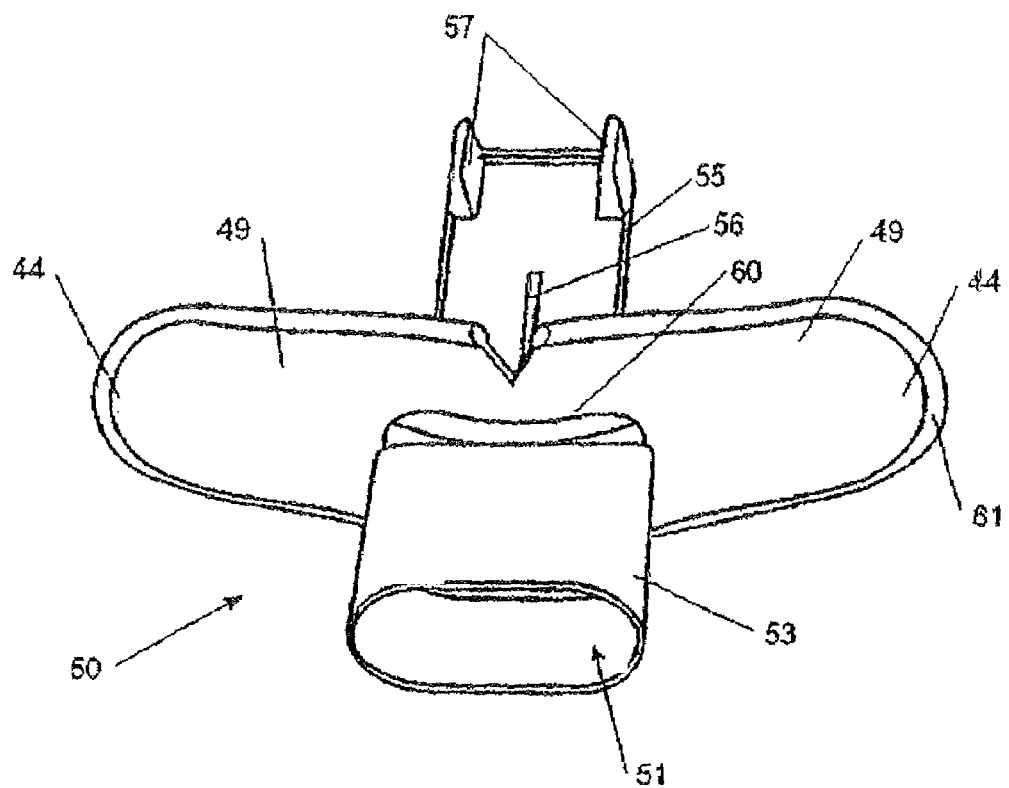
FIG. 4 is a perspective view from above of a mouthpiece that may be used with the elbow connector of the present invention.
Figure 5:
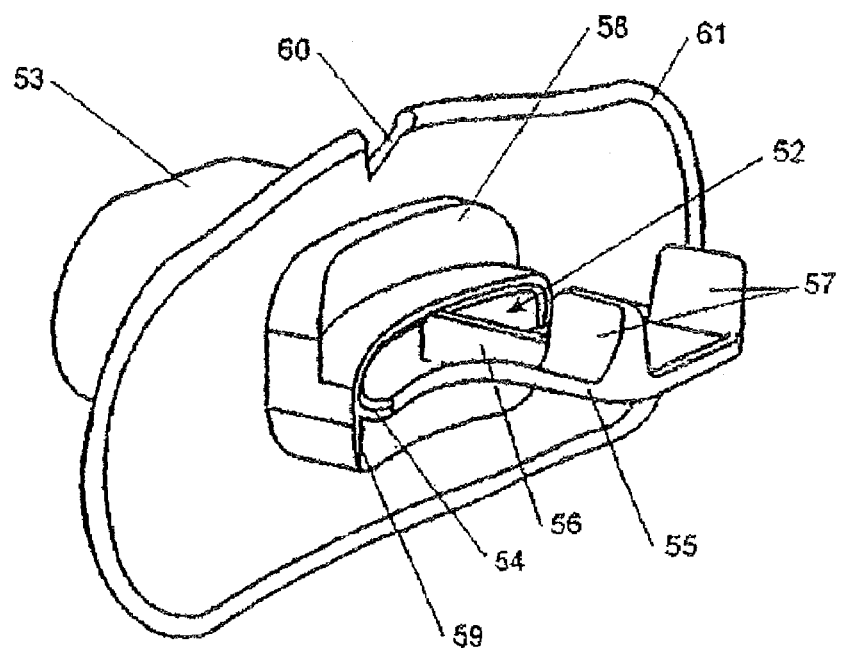
FIG. 5 is a perspective view from one side and from an inward direction of the mouthpiece of FIG. 4.
Figure 7:
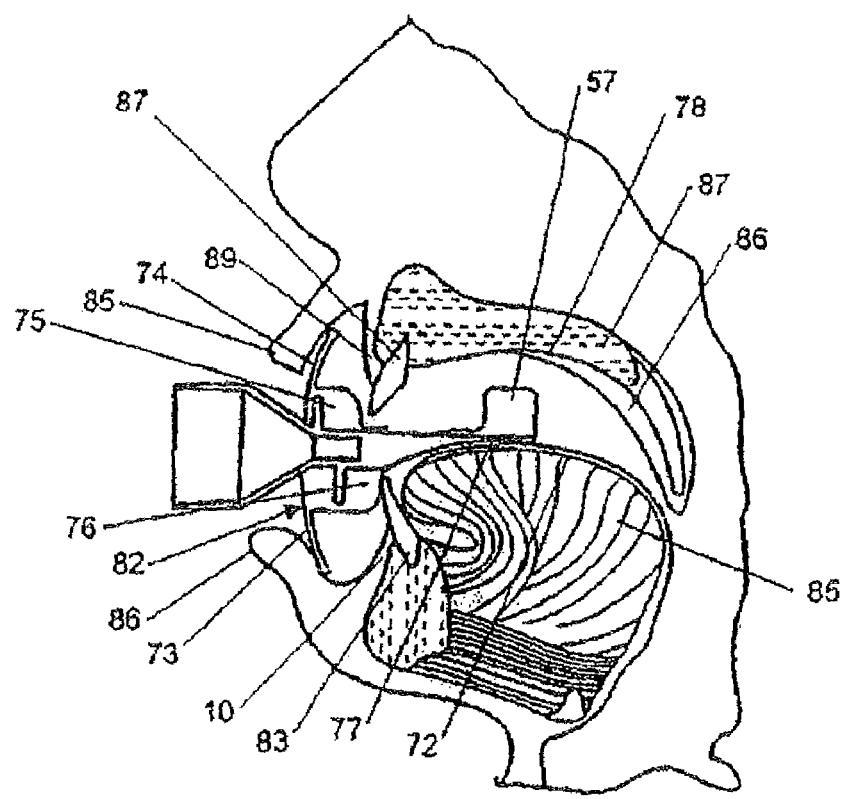
FIG. 7 is a cross-sectional view of the mouthpiece of FIG. 4 and a user with the mouthpiece in place to demonstrate the location and positioning thereof in relation to the main features of the patient's anatomy.

Referring now to FIG. 7, use of the mouthpiece according to FIGS. 4 to 6 is depicted. With the present mouthpiece 50, the upper and lower lips 85, 86 are further distended by the abutment action of the abutments 75, 76 against the upper and lower teeth 87, 88 respectively, thus forming a seal of greater pressure between the lips 85, 86 and the upper and lower portions respectively of the vestibular shield 49. A lower face 77 of the tongue depressor 55 impinges if necessary on the upper surface 72 of the tongue 85 and retains the tongue in the lower portion of the mouth. This ensures a clear gases outlet 52 from the gases passageway through the vestibular shield. The vertically extending spacers 57, if forced by pressure from the tongue, will engage against the roof of the patient's mouth and maintain a clear air passageway. This stops the sleeping patient unconsciously blocking the oral passageway and reverting to nasal breathing.

Figure 8:
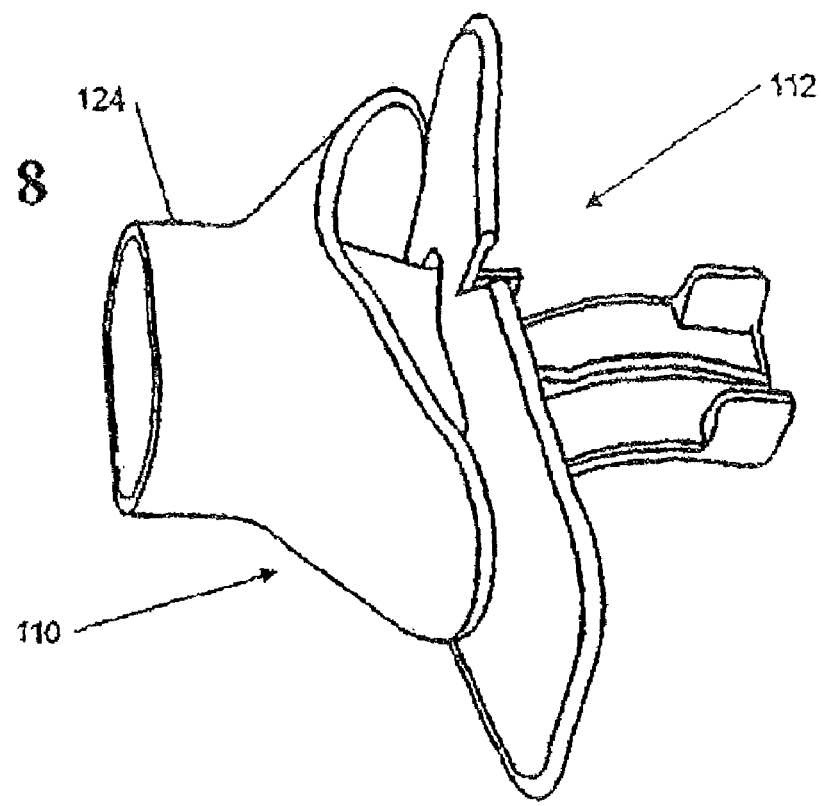
FIG. 8 is a perspective view of the mouthpiece with an outer flap in place.

Referring now to FIG. 8 of the present invention is illustrated including an extra-oral sealing flap 110. The flap 110 in its natural bias is tapered, the wide-open end of which is shaped to conform to the facial contours around the outside of the mouth of a user. The narrow end joins to a cylindrical section, which is designed to slide over the inlet port 114 of the mouthpiece 112. While this is one method of attachment the flap 100 might also be constructed as an integral part of the mouthpiece 112. The flap 110 needs to be constructed of flexible material. Therefore, materials such as silicone rubber can be employed to fashion the flap.

Figure 9:
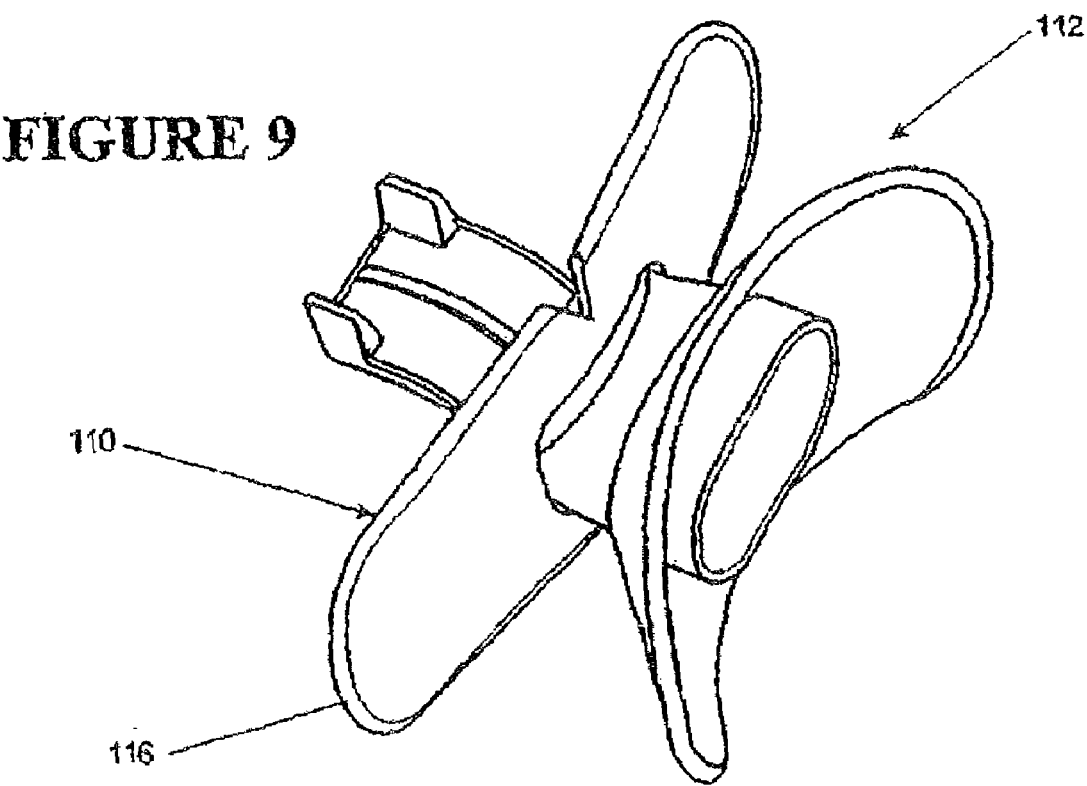
FIG. 9 is a perspective view of the outer flap bent back.

The outer flap 110 is seen in FIG. 9, in a bent back position. It will be appreciated that when the mouthpiece 112 is being inserted into the mouth of a users the outer flap 110 is intended to be in this bent back position to aid insertion. Prior to insertion, the outer flap is bent back by simply pressing on its outer periphery 116, until it snaps into the bent back position, in which it will stay unaided.

Figure 10:
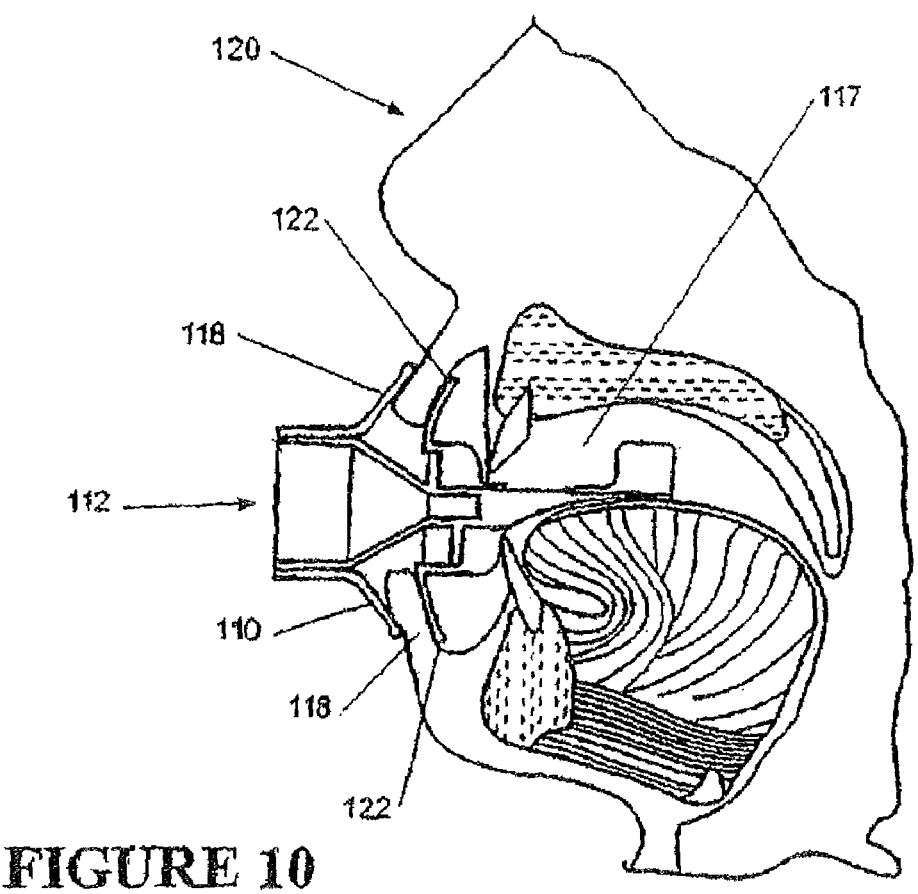
FIG. 10 is a cutaway view of the mouthpiece with the outer flap in use.

In FIG. 10 we see the outer flap 110 in use with the mouthpiece 112 in the mouth 117 of a user 120. Once correctly positioned in the mouth 116, the outer flap 110 may be adjusted into its operational position by pressing on its outer periphery 116 until it snaps back to press against the outside of the mouth 118. Due to the relative position of the vestibular shield 122 and the outer flap 110, the outer flap 110 is unable to fully reach its natural bias and thereby inflicts a compressive force on the outside of the mouth 118.

It will be appreciated that as well as providing a substantially airtight seal the addition of the outer flap provides enough compressive force on the mouth to keep the mouthpiece and conduit in place without the need for straps. This allows the administering of positive airway pressure ventilation therapy to be considerably less obtrusive than traditional methods.

Figure 11:
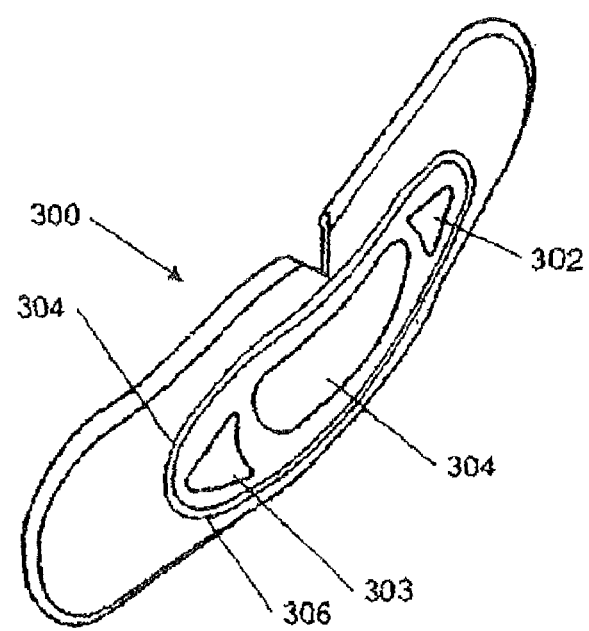
FIG. 11 is a perspective view of the outer flap including the ventilation apertures and moisture barrier.
Figure 12:
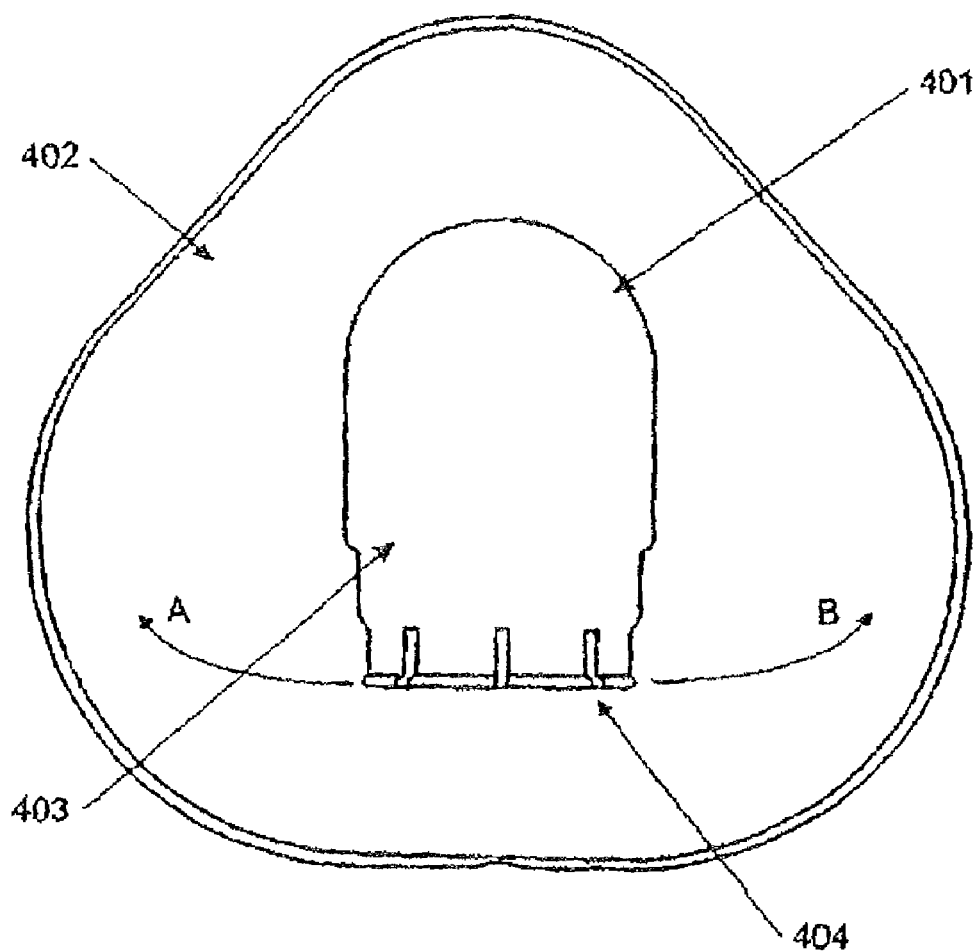
FIG. 12 is a front view of a nasal mask, including a swivelled elbow connection of the present invention.

In a further additional improvement shown in FIG. 11, the outer flap 300 is shown in perspective. Included are ventilation apertures 302, 303 either side of the gases port 304, which are surrounded by a ridge 306 acting as a moisture barrier. The apertures 302, 303 are provided such that any excess moisture leaking from the mouth will migrate to the apertures where they may evaporate. Small vents in the conduit may be used to direct small amounts of pressurised gas at the apertures to aid evaporation. The ridge 306 is included to ensure that no moisture migrates further into the sealing region 308, as this would be detrimental to the sealing properties of the flap.

Interface Connection

Figure 3:
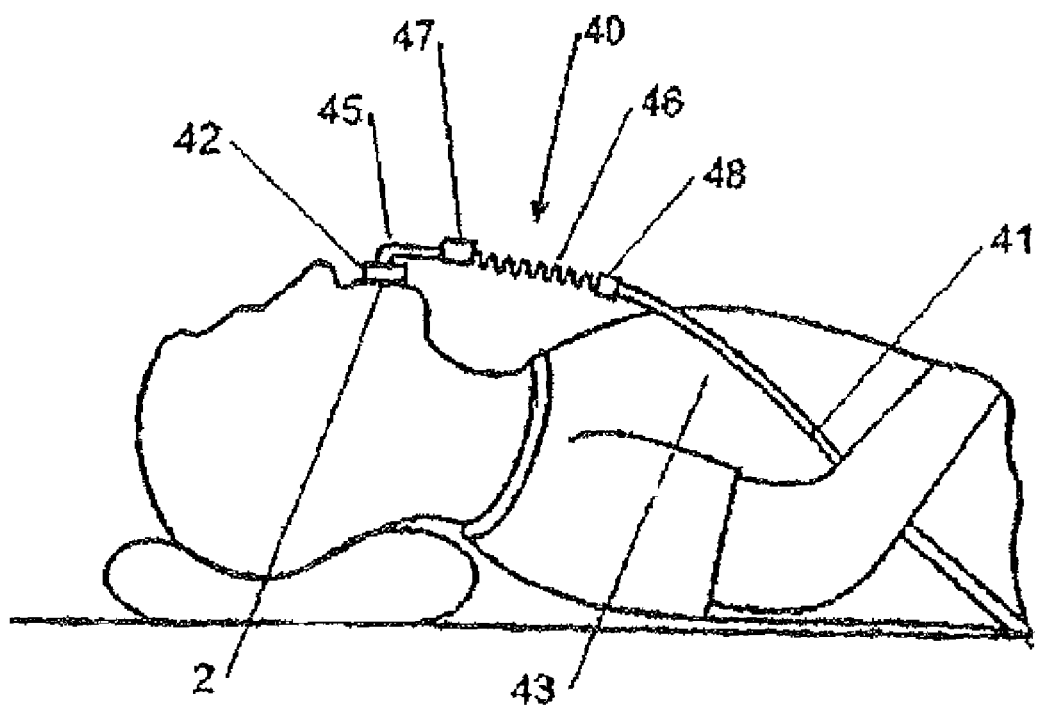
FIG. 3 is a side elevation view of an example of a connector used with a breathing circuit.

Attention is now directed to FIG. 3. It has been found that an additional factor in the effectiveness of any patient interface 2, is the manner in which the interface is connected to the breathing circuit. The weight of the breathing circuit, and any attempted movement of one other of the breathing circuit and the interface 2 relative to the other, is one of the largest influences tending to dislodge the interface 2. It must be noted that the interface 2 must remain in position and maintain a seal during all sleep, when the user has no muscle tone.

The connection is usually provided between a breathing circuit and an interface 2, which decouples the interface 2 from the breathing circuit. This type of configuration is shown in FIG. 3, where the interface is a mouthpiece, although a nasal mask may be used in place of the mouthpiece. The connection 40 is effective in reducing the forces placed on the interface 2 by the breathing circuit 41 when the user moves around during sleep.

To connect between the gases outlet 42, which is vertical when the user is lying on his or her back, and the breathing circuit 41, which is generally horizontal, a L-shaped elbow connector 45 is incorporated in the connection 40. The elbow connector 45 may be incorporated in the interface 2. The elbow connector 45 is formed at a right angle and provides a positive pressure on the interface 2. The elbow connector 45 may include a swivel joint and may be disconnected from gaseous outlet 42. The connection 40 further includes a connecting tube 46 provided between the elbow 45 and the breathing circuit 41. The connecting tube 46 is preferably connected to the breathing circuit 41 by a swivel joint 48 for reasons described herein. The breathing circuit 41, while flexible, will necessarily be stiff enough to maintain its inter over comparatively long runs, while the flexible connecting tube 46, being only a short length, for example 10 centimetres, merely has to span between the patient's mouth and chest, and can thereby be made in a manner that would not be suitable for long runs. Furthermore, as a result of the short length of the connecting tube 46, the connecting tube 46 does not need to incorporate significant insulation or heating capability. The connecting tube 46 may be formed from a thin plastic membrane supported over helical or double helical or corrugated supporting ribs. In such a case, the support makes the connection tube 46 laterally flexible and resistant to torsion. The elbow swivel connector 45 allows for movement of the connection tube 46 relative to the interface 2. The swivel connector 48 allows for movement of the connection tube 46 relative to the breathing circuit 41. It is to be understood that one or both of the swivel joints 45, 48 could be eliminated, but the preferred embodiment includes elbow swivel connector 48.

Fixable Swivel Joint

The nasal mask or mouthpiece as described above can be provided with an improved L-shaped elbow connector similar to that described above. Referring to FIGS. 12 to 16 a L-shaped elbow 401 is fixed to the mask base 402 on the nasal mask although not shown in the Figures to inlet 51 of the mouthpiece 50. Hereinafter when reference is made to "mask body" or "mask base 402" it is intended to refer to either the mask body or inlet 51 of the mouthpiece. A portion 403 of the elbow connector can be rotated about a point X in the directions of arrows A and B. The elbow connector 401 is connectable at its end 404 to the breathing circuit or conduit 3 as described with reference to FIGS. 1 and 2. The connector 401 is designed to be fixed into one of two positions and is able to be fully removed from the mask base 402. If the connector 401 is assembled in a first position, it is able to freely swivel, as indicated by the arrows labelled A and B on FIG. 12. If the elbow is pushed into a second position, an area of interference prevents the connector from freely swivelling.

Figure 13:
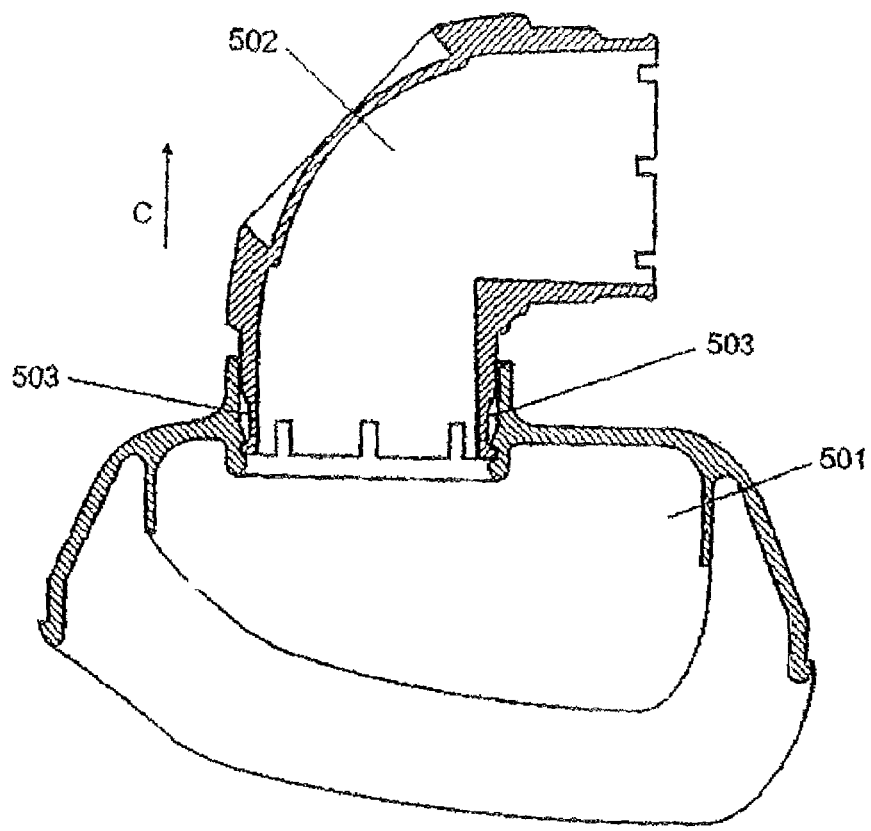
FIG. 13 is a side view of the swivelled elbow connection as attached to the mask body of the present invention in a first position.
Figure 14:
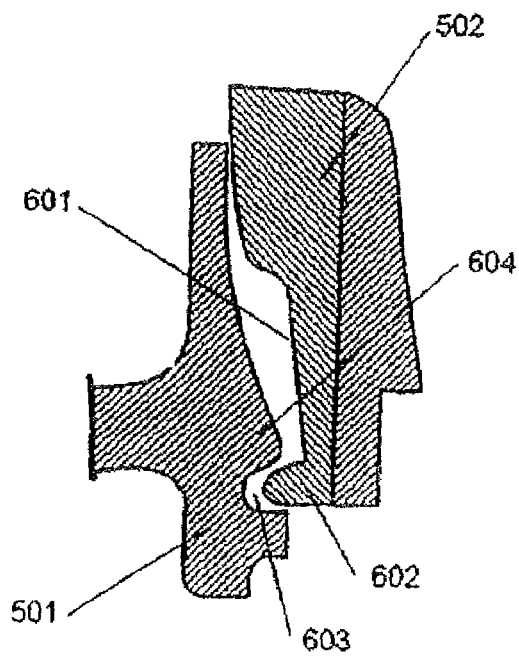
FIG. 14 is an exploded side view of the locking mechanism part of the swivelled elbow connection in the first position.

Attention is now drawn to FIGS. 13 and 14 where the mask body 501 and elbow connector 502 are shown in a first position where the connector 502 is able to freely rotate 360 degrees about a vertical axis out of the mask body. The connector 502 is connected to an aperture in the centre of the mask body, so that in use, gases flow from the breathing circuit through the elbow connector and aperture in the mask body and into the patient's lungs. The elbow connector 502 is held within the aperture in the mask body 501 by way of tubular connector 503 located on the arm of the elbow connector 502. The tubular connector 503 comprises various ridges and protrusions, moulded in the external surface of the elbow connector's arm, that meet with complimentary ridges and protrusions moulded in the interior surface of the aperture in the mask body (or the inlet 51 itself).

In particular, referring to FIG. 14, when the connector 502 is in the position as shown in FIG. 13, the ridge 601 and protrusion 602 in the connector 502 act with the small ridge 603 and protrusion 604 in the interior surface of the mask body, to lock the elbow connector 502 into a position that enables the elbow to swivel freely within the mask body. To remove the elbow 502 from the mask body 501 a force in the direction of arrow C (see FIG. 13) must be placed on the elbow so that the protrusion 602 on the elbow is forced past the protrusion 604 on the mask body, thereby releasing the connector 502 from the mask body.

Figure 15:
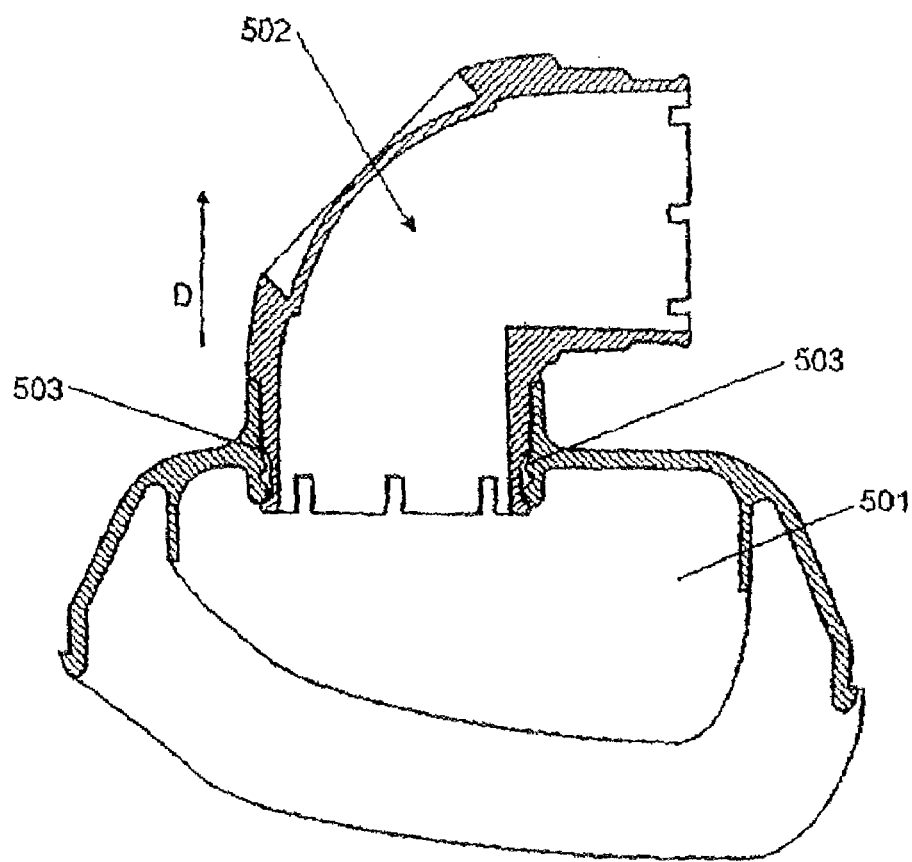
FIG. 15 is a side view of the swivelled elbow connection as attached to the mask body of the present invention, in a second position.
Figure 16:
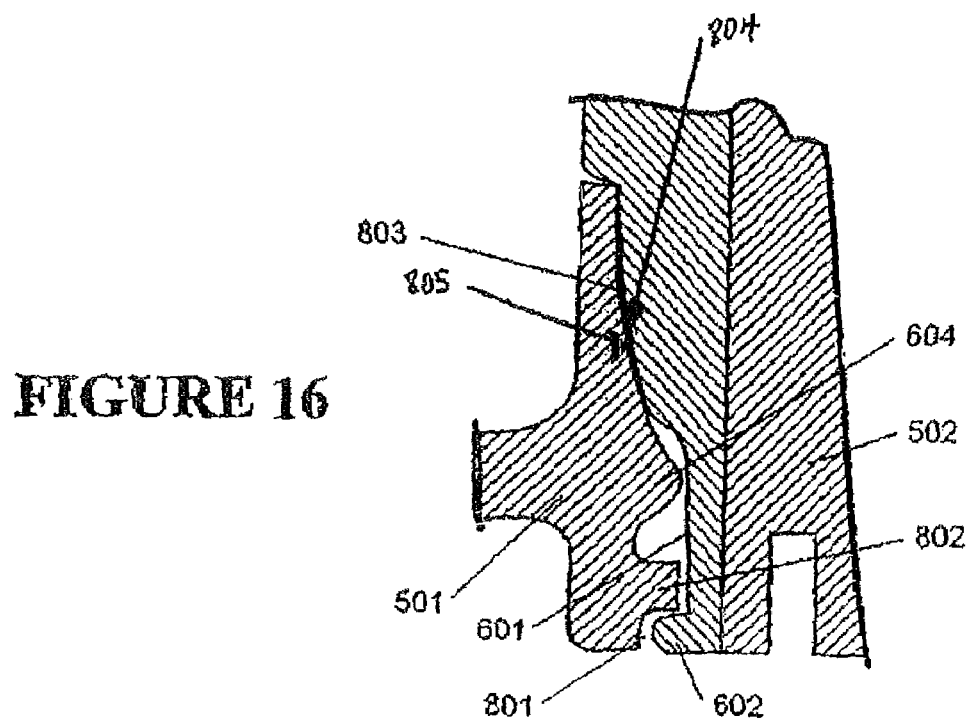

The elbow connector may be pushed downwards to into the mask body to a position as shown in FIGS. 15 and 16. Here, the protrusion 602 of the elbow has been pushed past the lower protrusion 802 on the mask body 501 and sits within a complimentary ridge 801 in the mask. The protrusion 604 on the mask abuts the ridge 601 on the elbow connector and the exterior side surface 804 of the elbow connector above the ridge 601 abuts the interior surface 805 of the mask aperture. The area of interference 803 between these surfaces prevents the elbow from freely swivelling within the mask.

The improvements, as described above, to the elbow connector of the present invention provides an attachment that can either freely rotate, or be locked in a particular position according to the patient's desires. The improvement to the prior art swivel connectors is that the short flexible tubing (46 as described with reference to FIG. 3) is no longer required.

Flow Diffuser and Bias Flow Directional Funnel

In an alternative form of the present invention, and in order to reduce the noise caused by expiratory gases being expelled from the mask or mouthpiece, either may be provided with an elbow connector having a diffuser. In prior art systems the flow diffuser is usually provided within the elbow connector at the point of connection to the mask body or inlet to the mouthpiece, in the present invention it is envisaged to provide a diffuser on the elbow connector. The following description refers to nasal mask when describing the diffuser. The diffuser may also be provided with an elbow connector used with a mouthpiece as previously described.

Figure 17:
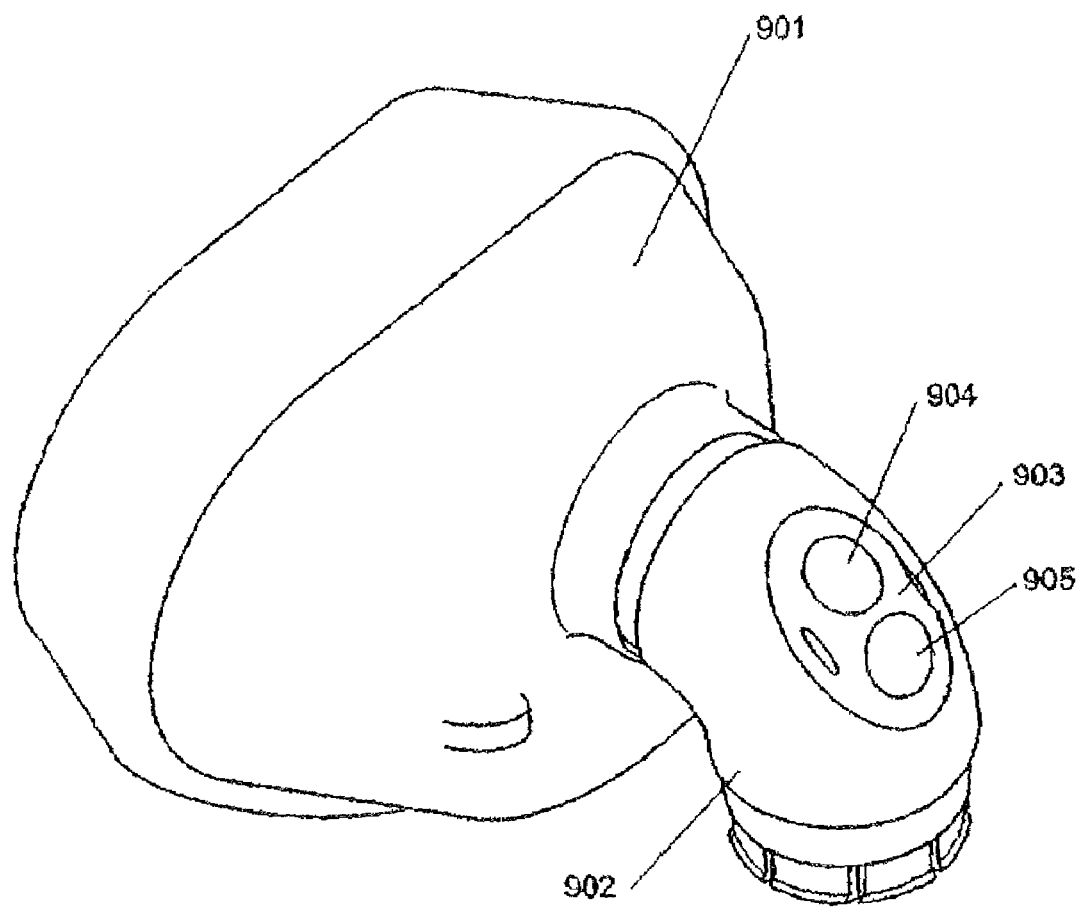
FIG. 17 shows a nasal mask body and elbow connector with diffuser.

FIG. 17 shows a nasal mask 901 and elbow connector 902 as that has a diffuser located along the length of the connector 902 previously. The elbow connector 902 includes a diffuser 903 on its exterior surface, the diffuser is a duct that provides for the broadening of the airflow and reduction in the airflow speed. In the preferred form the duct has outlet vent holes 904, 905 and the duct is made out of flexible rubber material. Note must be made that any number of vent holes may be provided in the duct, the preferred form shown in FIG. 17, merely shows two vents. The duct is preferably provided with a bias flow directional funnel, which will be described below.

Figure 19:
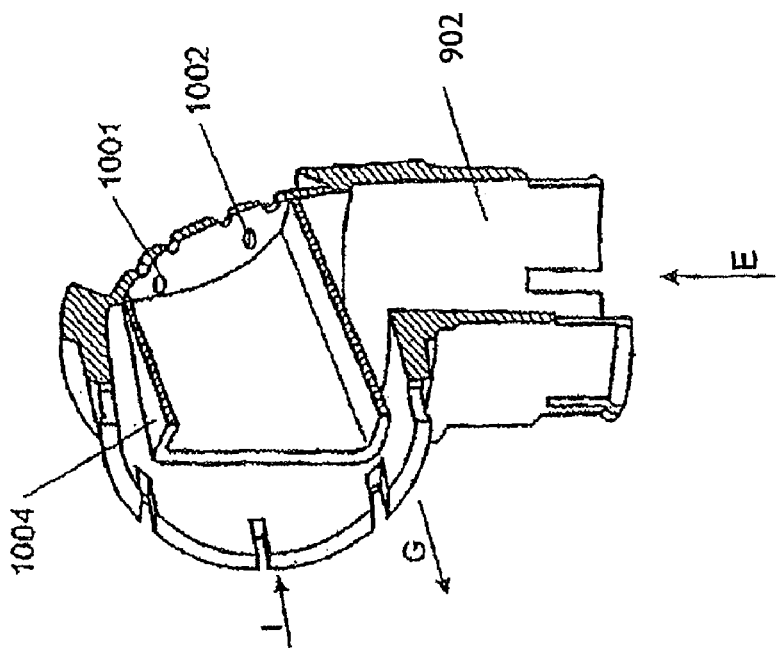
FIG. 19 shows a cutaway perspective view of the bias flow director of the present invention.
Figure 18:
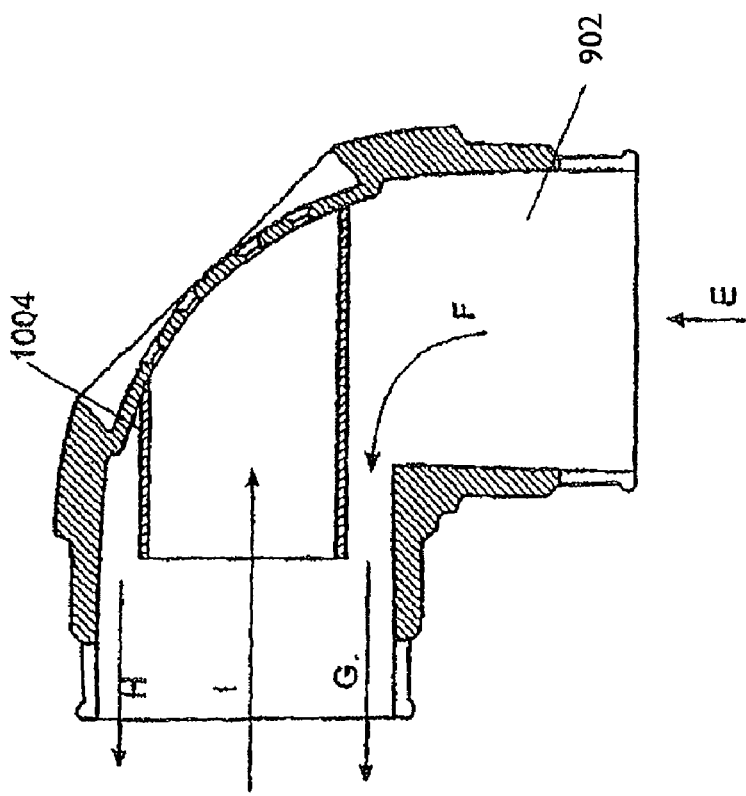
FIG. 18 shows a cutaway side view of the bias flow director of the present invention.

Referring to FIGS. 18 and 19, during positive pressure ventilation treatment a portion of the inlet air flow breathed by the patient is exhausted directly through the bias holes 1001, 1002. The only venting required is to clear the expired $CO_2$ gas from within the elbow connector 902. Therefore a funnel 1004 is provided within the elbow connector 902 that directs the exhaled $CO_2$ gases to the bias holes 1001, 1002 but does not direct the inlet airflow from the ventilation machine out the bias holes.

The purpose of the funnel is to vent exhaled air from the breathing system to remove $CO_2$ gases. With the prior art breathing systems it has been found that there is continuous leaking of gases through the vent holes during inspiration and expiration by the patient. Therefore, a loss of pressure occurs due to escaping air. Thus, on inspiration the patient receives less pressure and thus less breathing therapy, and therefore this requires that vent holes are provided that are as small as possible to lessen this effect.

During expiration by the patient it is preferred that most of the exhaled gases are vented through the vent holes, in order to prevent pressure spikes and to ensure $CO_2$ gases are expelled from the breathing tubing. The funnel therefore provides for shielding of the vent holes during inspiration, but enhances the venting of $CO_2$ gases by providing directional flows during expiration, this also allows for vent holes to be increased in size, providing larger exhaust areas.

Inlet airflow E flows from the ventilating system through the elbow connector 902 in the direction of arrows F, G and H and into the patient's lungs. The air that is exhaled, as indicated by arrow I, flows through the funnel 1004 that has been moulded within the interior of the elbow connector 902. The funnel 1004 is tubular in shape and provides for the funnelling of the exhausted $CO_2$ gases through the outlet bias holes 1001,1002. In use, the elbow connector 902 takes the place of elbow connector 45 which is shown in FIG. 3. Therefore, in use, the funnel 1004 is located in and extends along the portion of the elbow connector 902 which is substantially vertical when the patient is lying on his or her back wearing the patient interface 2.

Providing such a diffuser on the elbow connector effectively minimises the noise generated by the outward flow of expiratory gases from the mask. The diffuser of the present invention requires little or no maintenance and improves user comfort. The providing of a directional funnel within the elbow connector further minimises noise and reduces pressure spikes during exhalation.

The invention claimed is:

1. A patient interface for use as part of a system for delivering a supply of gases to a user, the patient interface comprising:
a hollow body adapted to locate onto a face of the user in use, said hollow body comprising an inside, an outside and an aperture passing from said inside of said hollow body to said outside of said hollow body,
an elbow connector adapted to connect between said aperture and the supply of gases so that in use said inside of said hollow body is in fluid communication with the supply of gases through said elbow connector,
said elbow connector comprising a funnel located within said elbow connector, said elbow connector comprising as least one outlet bias hole, said funnel adapted so that in use a substantial portion of gases expired from the user pass through said funnel and pass out of said patient interface through said at least one outlet bias hole, and
said funnel shielding said at least one outlet bias hole from an inlet flow of gases supplied to the user, said funnel located in and extending along a portion of said elbow connector that is substantially vertical when the user is lying on his or her back wearing said patient interface, said funnel extending from said at least one bias vent hole to a point at or close to a connection between said elbow connector and said hollow body,
said funnel fixed against rotation within said elbow connector.

2. A patient interface as claimed in claim 1 wherein said elbow connector is adapted to locate in said aperture in use and connect with said hollow body, said elbow connector and said hollow body further adapted so that in use said elbow connector can be swiveled relative to said hollow body.

3. A patient interface as claimed in claim 2 wherein said elbow connector further comprises a flexible duct portion on the exterior surface of said elbow connector over and around said at least one outlet bias hole, at least one outlet vent hole formed in said flexible duct portion.

4. A patient interface as claimed in claim 3 wherein said patient interface is a nasal mask.

5. A patient interface as claimed in claim 3 wherein said patient interface is a mouthpiece.

6. A patient interface for use as part of a system for delivering a supply of gases to a user, the patient interface comprising:
a hollow body adapted to locate onto a face of the user in use, said hollow body comprising an inside, an outside, and a rigid portion that comprises an aperture passing from said inside of said hollow body to said outside of said hollow body;
a mask cushion portion connected to said hollow body and in use adapted to substantially seal against the face of the user;
an elbow connector located in said aperture so that in use said inside of said hollow body is in fluid communication with the supply of gases through said elbow connector, said elbow connector able to swivel relative to said hollow body,
said elbow connector comprising a funnel located within said elbow connector, said elbow connector comprising at least one outlet bias hole, said funnel adapted so that in use a substantial portion of gases expired from the user pass through said funnel and pass out of said patient interface through said at least one outlet bias hole, and
said funnel shielding said at least one outlet bias hole from gases supplied to the user by the supply of gases, said funnel extending from said at least one bias vent hole to a point at or close to a connection between said elbow connector and said hollow body,
said funnel fixed against rotation within said elbow connector.

7. A patient interface as claimed in claim 6, wherein said patient interface is a nasal mask and said elbow connector further comprises a flexible duct portion on an exterior surface of said elbow connector over and around said at least one outlet bias hole, at least one outlet vent hole being formed in said flexible duct portion.

8. A patient interface as claimed in claim 6, wherein said funnel comprises a tubular extension extending from within said elbow connector from said at least one outlet bias hole.

9. A patient interface as claimed in claim 6, said funnel being substantially vertical when the user is supine and wearing said patient interface.

10. A patient interface for use as part of a system for delivering a supply of gases to a user, the patient interface comprising:
a hollow body adapted to locate onto a face of the user in use, said hollow body comprising an inside, an outside and an aperture passing from said inside of said hollow body to said outside of said hollow body,
an elbow connector adapted to connect between said aperture and the supply of gases so that in use said inside of said hollow body is in fluid communication with the supply of gases through said elbow connector,
said elbow connector comprising a funnel located within said elbow connector, and said elbow connector comprising as least one outlet bias hole, said funnel adapted so that in use a substantial portion of gases expired from the user pass through said funnel and pass out of said patient interface through said at least one outlet bias hole,
said funnel extending within said elbow connector and shielding said at least one outlet bias hole from an inlet flow of gases supplied to the user, said funnel molded within an interior of said elbow connector, said funnel located in and extending along a portion of said elbow connector that is substantially vertical when the user is laying on a back of the user wearing said patient interface, said funnel extending from said at least one bias vent hole to a point at or close to a connection between said elbow connector and said hollow body wherein said elbow connector is adapted to locate in said aperture in use and connect with said hollow body, said elbow connector and said hollow body further adapted so that in use said elbow connector can be swiveled relative to said hollow body and wherein said elbow connector further comprises a flexible duct portion on an exterior surface of said elbow connector over and around said at least one outlet bias hole, at least one outlet vent hole formed in said flexible duct portion.

11. A patient interface as claimed in claim 10, wherein said patient interface is a nasal mask.

12. A patient interface as claimed in claim 10, wherein said patient interface is a mouthpiece.

13. A patient interface for use as part of a system for delivering a supply of gases to a user, the patient interface comprising:
- a hollow body adapted to locate onto a face of the user in use, said hollow body comprising an inside, an outside, and a rigid portion that comprises an aperture passing from said inside of said hollow body to said outside of said hollow body;
- a mask cushion portion connected to said hollow body and in use adapted to substantially seal against the face of the user;
- an elbow connector located in said aperture so that in use said inside of said hollow body is in fluid communication with the supply of gases through said elbow connector, said elbow connector able to swivel relative to said hollow body,
- said elbow connector comprising a funnel located within said elbow connector, said elbow connector comprising at least one outlet bias hole, said funnel adapted so that in use a substantial portion of gases expired from the user pass through said funnel and pass out of said patient interface through said at least one outlet bias hole, and
- said funnel extending within said elbow connector and shielding said at least one outlet bias hole from gases supplied to the user by the supply of gases, said funnel molded within an interior of said elbow connector that is substantially vertical when the user is lying on a back of the user wearing said patient interface, said funnel extending from said at least one bias vent hole to a point at or close to a connection between said elbow connector and said hollow body,
- wherein said patient interface is a nasal mask and said elbow connector further comprises a flexible duct portion on an exterior surface of said elbow connector over and around said at least one outlet bias hole, at least one outlet vent hole being formed in said flexible duct portion.

14. A patient interface comprising:
- a hollow body comprising an inside, an outside and an aperture passing from said inside of said hollow body to said outside of said hollow body;
- a mask cushion portion connected to said hollow body and adapted to be placed against a face of a user;
- an elbow connector comprising a first portion and a second portion wherein said first portion is substantially perpendicular to said second portion, said first portion being disposed in line with said mask portion, said elbow connector comprising at least one outlet bias hole disposed at a point at or near a location where said first portion and said second portion meet;
- a funnel located within said elbow connector and extending from a location within said elbow connector and ending at or near said at least one bias hole, said funnel fixed against rotation within said elbow connector;
- said funnel shielding said at least one outlet bias hole and said funnel substantially overlying said second portion of said elbow connector.

15. The patient interface as claimed in claim 14, wherein said at least one bias hole is adapted to allow an airflow out of the patient interface.

16. The patient interface as claimed in claim 14, wherein said elbow connector comprises at least two distinct gases-flow pathways.

17. The patient interface of as claimed in 16, wherein said at least two distinct gases-flow pathways comprise a first gases-flow pathway adapted to allow an inspiratory flow of gases towards said mask portion and a second gases-flow pathway adapted to allow a distinct flow of expiratory gases away from said mask portion.

18. The patient interface as claimed in claim 17, wherein said second gases-flow pathway comprises an interior of said funnel.

19. The patient interface as claimed in claim 18, wherein the first gases-flow pathway does not comprise said interior of said funnel.

20. A patient interface as claimed in claim 14, wherein said elbow connector further comprises a flexible duct portion on an exterior surface of said elbow connector over and around said at least one outlet bias hole, and said flexible duct portion comprises at least one outlet vent hole formed in said flexible duct portion.

21. A patient interface as claimed in claim 20, wherein said flexible duct portion comprises a rubber material.

* * * * *